(12) United States Patent
Katta

(10) Patent No.: US 8,636,953 B2
(45) Date of Patent: Jan. 28, 2014

(54) SURFACE ACOUSTIC WAVE SENSING DEVICE

(71) Applicant: Kyocera Corporation, Kyoto (JP)

(72) Inventor: Hiroshi Katta, Kyoto (JP)

(73) Assignee: Kyocera Corporation, Kyoto (JP)

( * ) Notice: Subject to any disclaimer, the term of this patent is extended or adjusted under 35 U.S.C. 154(b) by 0 days.

(21) Appl. No.: 13/853,039

(22) Filed: Mar. 28, 2013

(65) Prior Publication Data
US 2013/0259746 A1  Oct. 3, 2013

(30) Foreign Application Priority Data
Mar. 28, 2012 (JP) ................................. 2012-073528

(51) Int. Cl.
*H01L 27/20* (2006.01)

(52) U.S. Cl.
USPC ........... 422/68.1; 422/69; 422/98; 310/313 R; 310/311

(58) Field of Classification Search
USPC .................. 422/68.1, 69, 98; 310/313 R, 311
See application file for complete search history.

(56) References Cited

U.S. PATENT DOCUMENTS

| 7,331,236 | B2 * | 2/2008 | Smith et al. ..................... 73/703 |
| 2002/0125792 | A1 * | 9/2002 | Tabota ....................... 310/313 R |
| 2008/0084135 | A1 * | 4/2008 | Ramsesh et al. .......... 310/313 R |
| 2008/0230859 | A1 * | 9/2008 | Zaghloul et al. .............. 257/428 |

FOREIGN PATENT DOCUMENTS

JP         2008122105 A     5/2008

* cited by examiner

*Primary Examiner* — Monique Cole
(74) *Attorney, Agent, or Firm* — Duane Morris LLP

(57) ABSTRACT

A SAW sensor includes a substrate, first and second IDT on the substrate and a detector portion between the first and second IDT. The first IDT generates a surface acoustic wave in response to a high-frequency signal input. The second IDT receives the SAW from the first IDT, and converts the SAW to an electric signal and outputs the electric signal. A one pulse signal, which is input to the first IDT electrode, has an applying time that is at least as long as a delay time of a surface acoustic wave at the detector less an arrival time of a direct wave attributable to electromagnetic coupling between the first IDT and the second IDT electrode, and that is less than an arrival time at the second IDT of a third response wave of the surface acoustic wave from the first IDT.

7 Claims, 11 Drawing Sheets

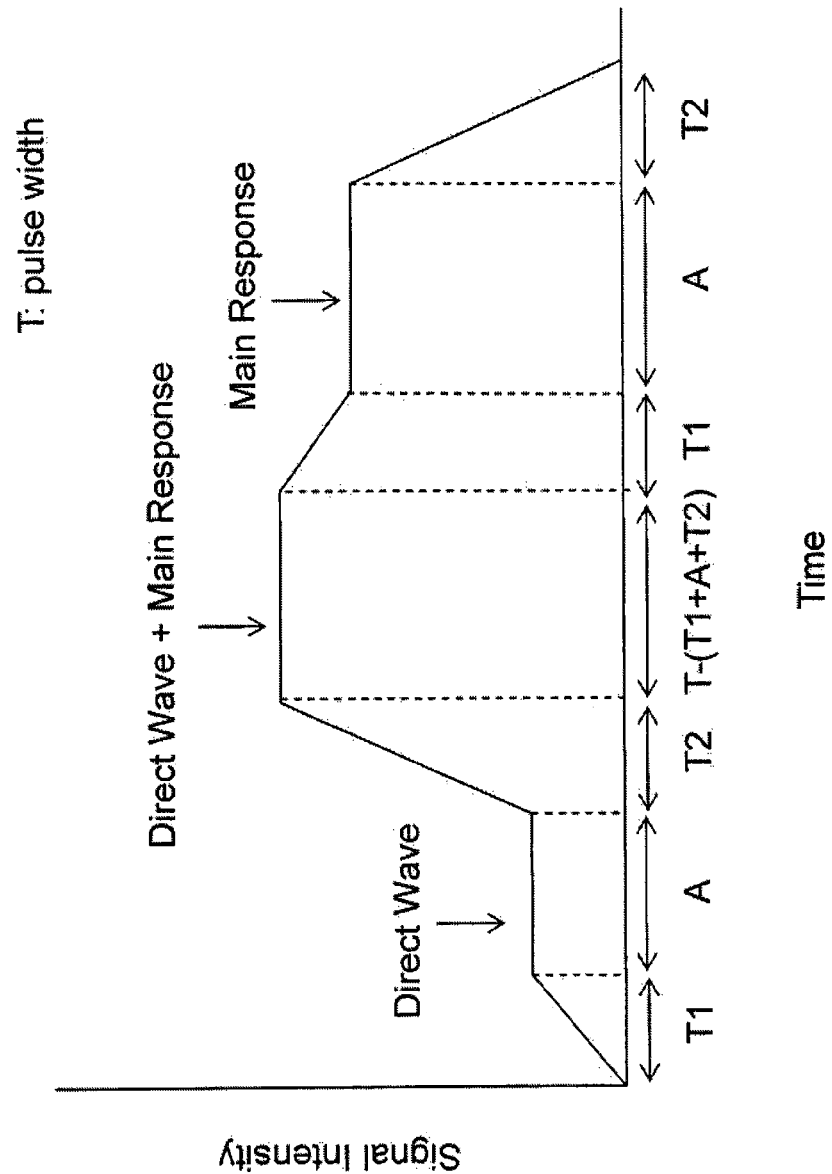

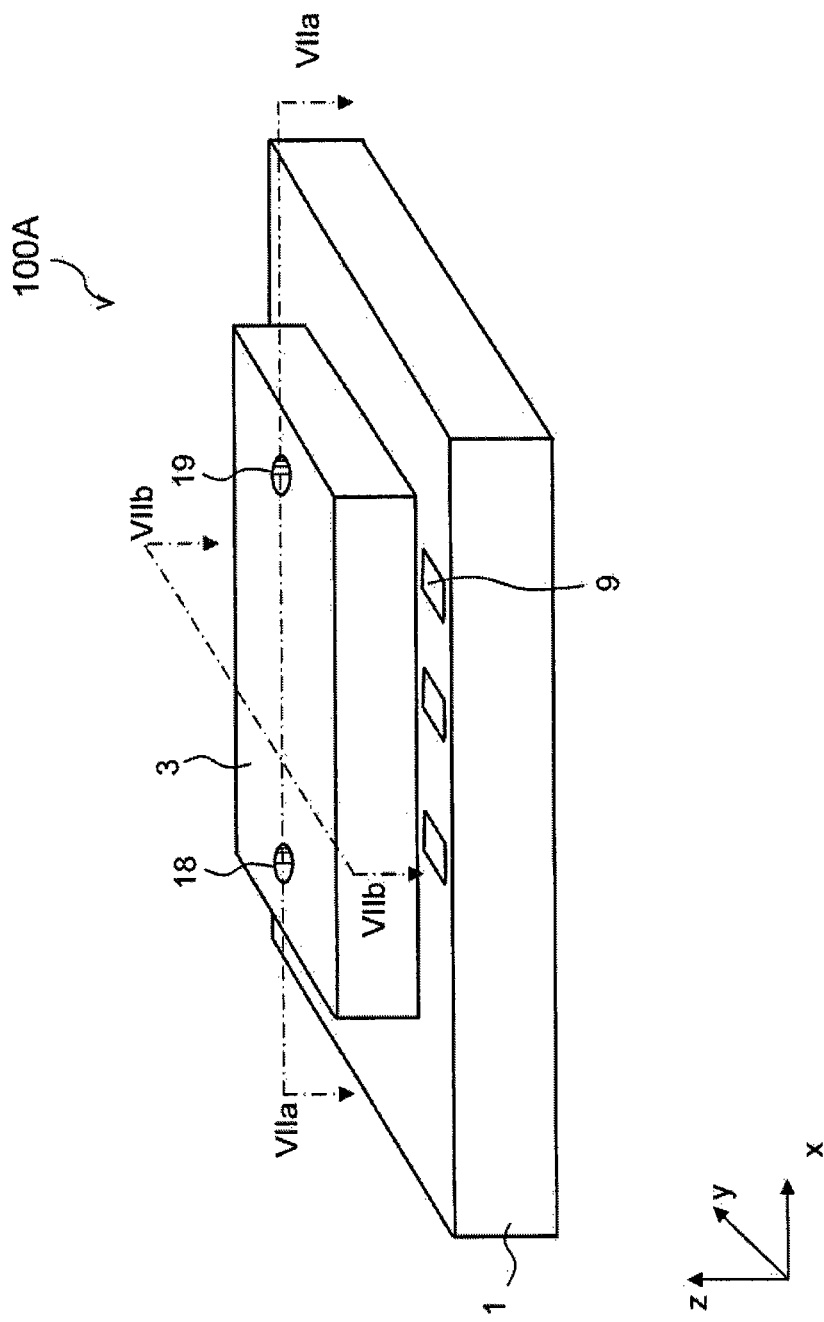

SURFACE ACOUSTIC WAVE SENSING DEVICE

CROSS-REFERENCE TO RELATED APPLICATION

The present application claims the priority rights of Japanese Patent Application No. 2012-073528 filed on Mar. 28, 2012, and incorporates herein the entire disclosure of the application for reference.

FIELD

The present invention relates generally to SAW sensors and SAW sensing devices, and particularly relates to SAW sensors and SAW sensing devices for measuring liquid properties or substances contained within liquids.

BACKGROUND

Known SAW (surface acoustic wave) sensors employ SAW elements to measure properties and/or components of liquid specimen. Such sensors measure specimen concentration through detection of SAW phase difference. A SAW sensor or SAW sensing device that would permit detection of a signal with good sensitivity is desired.

SUMMARY

Disclosed are a SAW sensor and a SAW sensing device. The SAW sensor includes first and second IDT (Inter digital transducers) and a detector portion between the first and the second IDT. A one pulse signal, which is input to the first IDT, has an applying time that is at least as long as a delay time of a surface acoustic wave at the detector less an arrival time of a direct wave attributable to electromagnetic coupling between the first IDT and the second IDT, and that is less than an arrival time at the second IDT of a third response wave of the surface acoustic wave from the first IDT.

In an embodiment, a SAW sensor includes a piezoelectric substrate; the first IDT disposed on a main surface of the piezoelectric substrate and configured to generate a surface acoustic wave when a high-frequency signal is applied thereto; the second IDT disposed on the main surface of the piezoelectric substrate and configured to receive the surface acoustic wave from the first IDT and to convert the received surface acoustic wave into an electrical signal that is output therefrom; and a detector portion disposed on the main surface of the piezoelectric substrate at a location thereof which is between the first IDT and the second IDT electrode, and configured to cause delay in the surface acoustic wave and to change in mass in correspondence to reaction with and/or sorption of a target provided in a specimen delivered thereto. The high-frequency signal is input to the first IDT as a one pulse signal having an applying time that is at least as long as a delay time of the surface acoustic wave at the detector portion less an arrival time of a direct wave attributable to electromagnetic coupling between the first IDT and the second IDT, and that is less than an arrival time at the second IDT of a third response wave of the surface acoustic wave from the first IDT electrode.

In another embodiment, a SAW sensing device includes a SAW sensor described above; and the high-frequency signal generating device that generates the one pulse signal.

BRIEF DESCRIPTION OF THE DRAWINGS

Embodiments of the present disclosure are hereinafter described in conjunction with the following figures, wherein like numerals denote like elements. The figures are provided for illustration and depict exemplary embodiments of the present disclosure. The figures are provided to facilitate understanding of the present disclosure without limiting the breadth, scope, scale, or applicability of the present disclosure.

FIG. 3A is a schematic graph showing a signal intensity when a pulse width of a one pulse is greater than an output response time.

FIG. 5 is a perspective view of an exemplary SAW sensor according to an embodiment of the disclosure.

DETAILED DESCRIPTION

Figure 1:
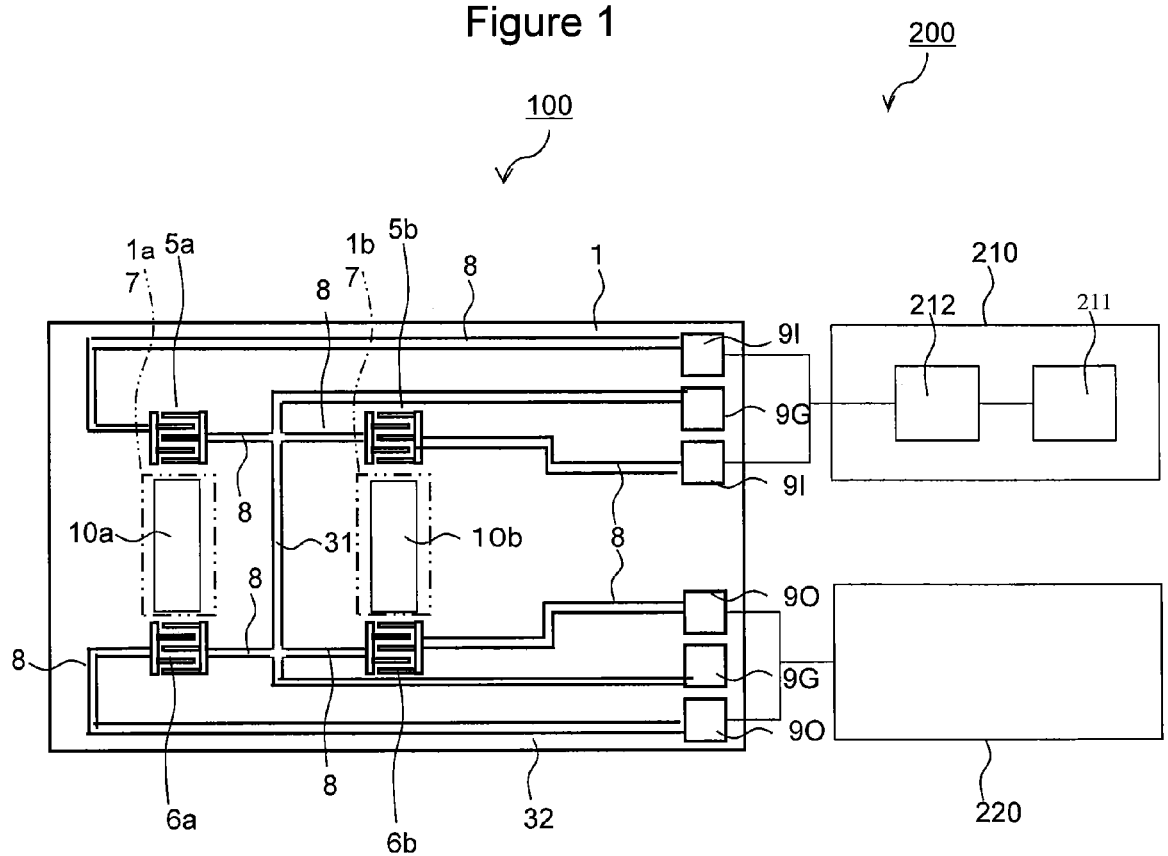
FIG. 1 is a schematic diagram showing a basic structure of an exemplary SAW sensing device according to an embodiment of the disclosure.

The following description is presented to enable a person of ordinary skill in the art to make and use the embodiments of the disclosure. The following detailed description is exemplary in nature and is not intended to limit the disclosure or the application and uses of the embodiments of the disclosure. Descriptions of specific devices, techniques, and applications are provided only as examples. Modifications to the examples described herein will be readily apparent to those of ordinary skill in the art, and the general principles defined herein may be applied to other examples and applications without departing from the spirit and scope of the disclosure. The present disclosure should be accorded scope consistent with the claims, and not limited to the examples described and shown herein.

Embodiments of the disclosure are described herein in the context of one practical non-limiting application, namely, a mobile electronic device such as a mobile phone. Embodiments of the disclosure, however, are not limited to such SAW sensors, and the techniques described herein may be utilized in other applications. For example, embodiments may be applicable to SAW sensor devices and the like. As would be apparent to one of ordinary skill in the art after reading this description, these are merely examples and the embodiments of the disclosure are not limited to operating in accordance with these examples. Other embodiments may be utilized and structural changes may be made without departing from the scope of the exemplary embodiments of the present disclosure.

In the descriptions of the drawings which follow, like components are assigned like reference numerals. Note that features such as component size and distance between/among components are shown in schematic fashion and may differ from actual dimensions.

While any direction may be considered up or down in a SAW sensor, for convenience of the description which follows, terminology such as top face, bottom face, and so forth will be employed in the context of a rectangular xyz coordinate system defined such that the positive z direction is taken to be up.

FIG. 1 is a schematic diagram showing basic structure of an exemplary SAW sensing device 200 according to an embodiment of the disclosure. At FIG. 1, schematic structure of respective parts is shown, some components having been omitted from the drawing. SAW sensing device 200 includes high-frequency signal generating device 210, SAW sensor 100, and electrical signal sampling means (unit) 220.

High-frequency signal generating device 210 has high-frequency signal generator (hereinafter "signal generator") 211 and high-frequency signal controller (hereinafter "signal controller") 212.

Signal generator 211 generates high-frequency signals. A Schottky diode, SAW signal generator, or the like may in an embodiment be employed as signal generator 211. Signal controller 212 is for switching to cause the high-frequency signal generated by signal generator 211 to be alternately applied and not applied to SAW sensor 100. An RF switch or the like may in an embodiment be employed as signal controller 212. A One pulse signal is defined as a high-frequency signal which is applied at SAW sensor 100 during the time between when applying of this high-frequency signal is switched on and off by signal controller 212.

SAW sensor 100 is provided piezoelectric substrate 1, first IDT (interdigitated transducers) 5 at the input side thereof, second IDT 6 at the output side thereof, and detector portion 7. The First IDT 5 and the second IDT 6 are disposed on a main surface of piezoelectric substrate 1. It will be convenient for purposes of description to define a first region 1a and a second region 1b which are respectively disposed between the first IDT 5 and the second IDT 6 as seen in a plan view. At these first and second regions 1a, 1b, the detector portion 7 (7a, 7b) is disposed directly above short-circuit electrodes 10a, 10b by way of intervening protective layer 4, described below.

The signal from high-frequency signal generating device 210 is applied by the first IDT 5, and the applied high-frequency signal causes production of a surface acoustic wave. More specifically, the first IDT 5 comprises pairs of mutually interdigitated electrodes. One of the pair of electrodes is electrically connected to high-frequency signal generating device 210 by way of land 9I and to signal line 8 which is formed on piezoelectric substrate 1. The other of the pair of electrodes is electrically connected to land 9G which is connected to reference potential ($v_{ref}$) and to signal line 8.

Surface acoustic wave which is produced by first IDT 5 and which propagate along the surface of piezoelectric substrate 1 are converted to an electrical signal by second IDT 6. More specifically, second IDTs 6 comprise pairs of mutually interdigitated electrodes. One of the pair of electrodes is electrically connected to electrical signal sampling means 220 by way of land 9I and to signal line 8 which is formed on piezoelectric substrate 1. The other of the pair of electrodes is electrically connected to land 9G which is connected to reference potential ($v_{ref}$) and to signal line 8.

Detector portion 7 is located between the first IDT 5 and the second IDT 6. Detector portion 7 is provided to delay SAW which is produced by the first IDT 5. A specimen which includes a target in liquid state is supplied on the detector portion 7. Detector portion 7 varies depending on sorption of target thereby and/or reaction of target therewith. Detailed mechanisms by which this may occur are described below.

Electrical signal sampling means 220, which is electrically connected to the second IDT 6, carries out sampling of the electrical signal output from the second IDT 6. By virtue of the fact that high-frequency signal generating device 210 and electrical signal sampling means 220 are electrically connected to SAW sensor 100, SAW sensing device 200 is constituted.

The high-frequency signal that is input to SAW sensor 100 will now be described. High-frequency signal generating device 210 generates a one pulse signal. This one pulse signal might be generated over an applying time that is at least as long as a time subtracted the arrival time of the direct wave attributable to electromagnetic coupling between the first IDT 5 and the second IDT 6 from the delay time in the surface acoustic waves at the detector portion 7. The one pulse signal might be generated over an applying time that is less than the arrival time at the second IDT 6 of the third response wave of the surface acoustic wave from the first IDT 5.

The one pulse signal which is generated is input to the first IDT 5 of the SAW sensor 100. By controlling the one pulse signal, it is possible to increase the sensitivity with which signal detection is carried out by SAW sensor 100. The reason that this is so will now be described. In the description which follows, the following conditions were used for an exemplary SAW sensor 100.

Number of pairs of electrode fingers at first and second IDT electrodes 5, 6, respectively: 25

IDT finger pitch: 5 μm (one-half of the wavelength of the surface acoustic wave)

Surface acoustic wave propagation speed: 4000 m/s

Surface acoustic wave wavelength: 10 μm

Center frequency: 411 MHz

Length of detector 7: Approximately 300λ (3 mm)

Delay time: 0.86 μsec

Figure 2A:
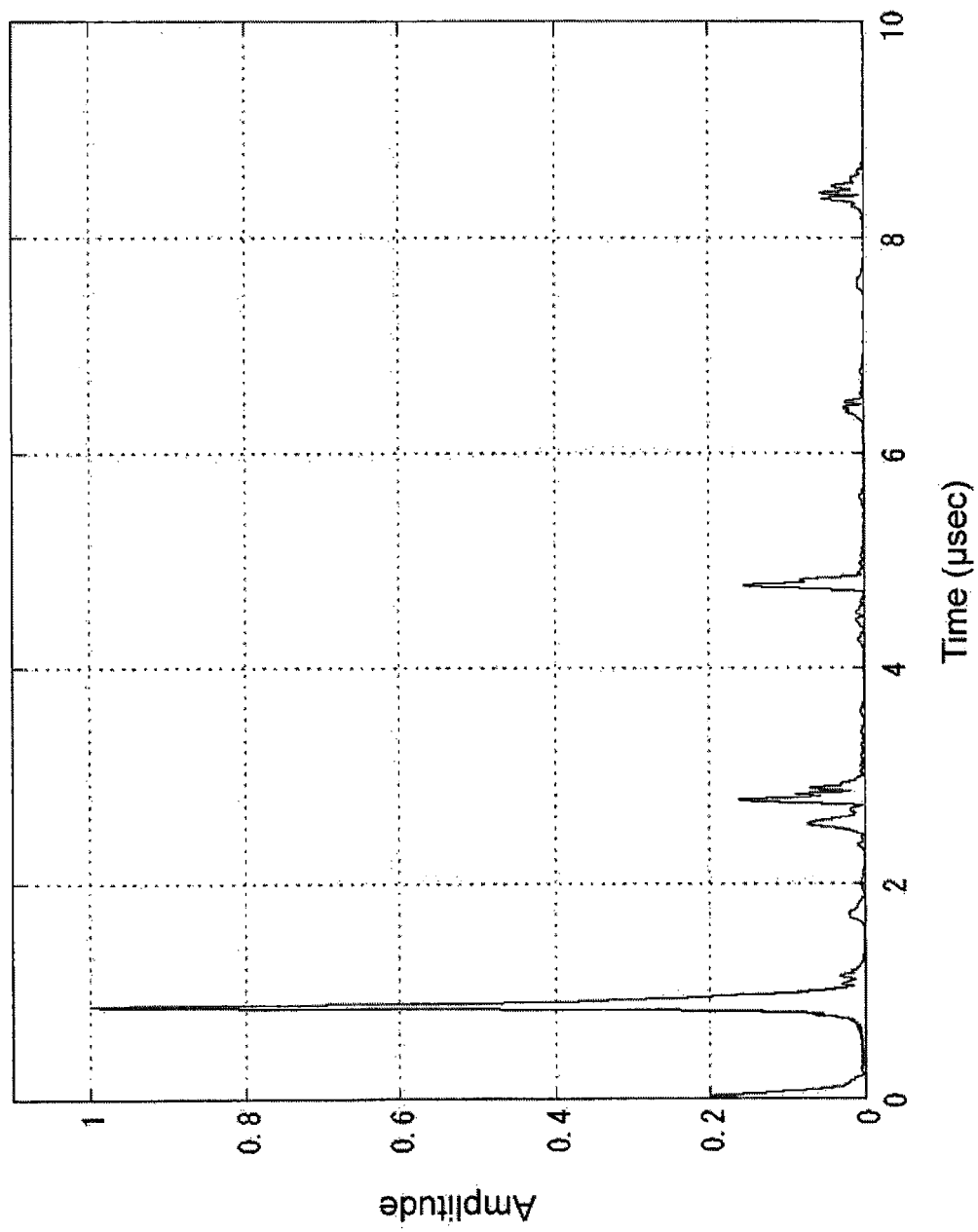
FIG. 2A is a graph showing outputs when a single pulse is input to a SAW sensor according to an embodiment of the disclosure.
Figure 2B:
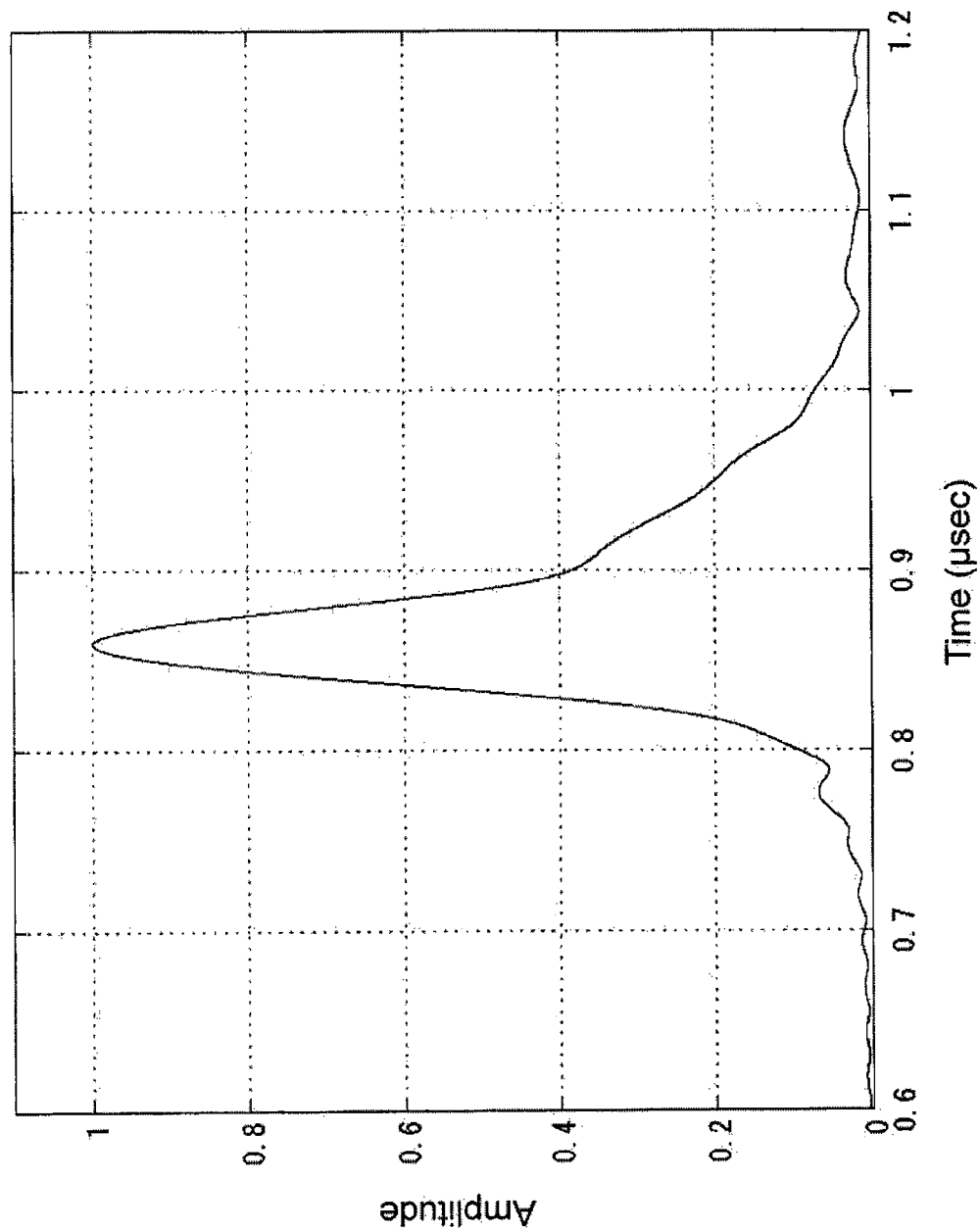
FIG. 2B is a diagram showing a portion of the graph of FIG. 2A.

The signal output from the second IDT 6 at the SAW sensor when a single pulse (burst signal) is input to the first IDT 5 is shown at FIGS. 2A and B. At FIGS. 2A and B, the horizontal axis is time (units=μsec), and the vertical axis shows amplitude characteristics normalized relative to a value of 1. FIG. 2A is a graph showing output when the single pulse is input to the SAW sensor; more specifically, amplitude characteristics are shown as a function of time for the period from 0 μsec to 6 μsec. FIG. 2B is a diagram showing a portion of the graph of FIG. 2A; more specifically, amplitude characteristics at FIG. 2A in the interval between 0.6 μsec and 1.2 μsec are shown against an expanded time scale at FIG. 2B.

As shown at FIGS. 2A and B, direct-wave signal components are generated at locations near the main response signal in the vicinity of 0.86 μsec. The direct wave is generated at 0 μsec, having arisen due to electromagnetic coupling between first IDT 5 and second IDT 6. This direct wave is of constant intensity, being unaffected by whether target(s) is/are present within the specimen and so forth. The full width at half maximum of the direct wave is taken to be the direct wave arrival time T1, the full width at half maximum of the main response signal is taken to be the single pulse width T2, and the time from the start of the single pulse width less the direct wave arrival time will for convenience of description be defined as the output response time A.

Figure 3B:
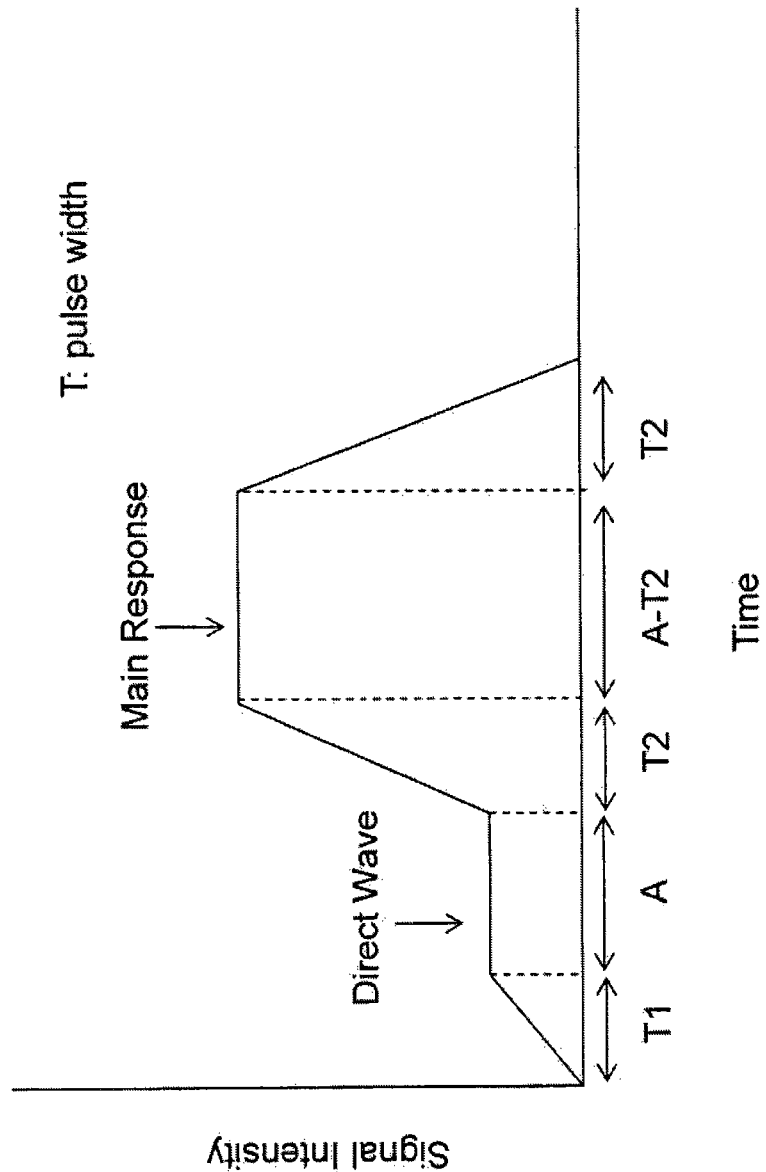
FIG. 3B is a graph showing output signal strength when a pulse width of a one pulse is less than or equal to an output response time.

FIGS. 3A and B are schematic graphs respectively showing signal intensity as a function of time for two different high-frequency signal applying times T. More specifically, FIG. 3A is a schematic graph showing a signal intensity when applying time T is long such that a pulse width of the one pulse signal is greater than the output response time, while FIG. 3B is a schematic graph showing a signal intensity when applying time T is short such that the pulse width of the one pulse signal is less than or equal to an output response time. While the amplitude and shape of the main response signal will vary depending on the state of detector portion 7 and so forth, the signal, which depends on the state of detector portion 7, may be accurately detected regardless of its amplitude. This being the case, as the single pulse signal burst) would be unstable, the burst may be generated in continuously so that the one pulse signal is provided to have an adequate signal width, and the one pulse signal will be input to SAW sensor 100 in adequate duration. More specifically, the pulse width of the one pulse signal may be greater than the output response time. When the pulse width is made to satisfy this condition, the electrical signal which is output from the second IDT 6 will resemble that shown at FIG. 3A. At FIG. 3A, because the pulse width of the one pulse signal exceeds the output response time, this makes it possible to reliably know the period during which it is possible to obtain information attributable only to the main response signal, without admixture of influence from the direct wave that is produced with each respective burst, and to properly identify this period as the output response time. In contradistinction hereto, it is preferred not to have a situation such as that shown at FIG. 3B, where high-frequency signal applying time is less than or equal to output response time, because this would tend to decrease the period during which it is possible to obtain information attributable only to the main response signal. At FIG. 3, note that whereas actual shape of the direct wave would resemble an exponential function due to its capacitive component, and actual shape of the main response wave would be triangle wave because it is a surface acoustic wave, these are for convenience shown as if they were rectangular waves. Furthermore, as shown at FIG. 2A, the pulse width of the one pulse signal may be less than the arrival time of the third response wave so as to eliminate the effect of the third response wave. That is, the pulse width of the one pulse signal may be not more than three times the delay time. Saying different words, the pulse width of the one pulse signal may be not more than the arrival time of the main response.

Figure 4A:
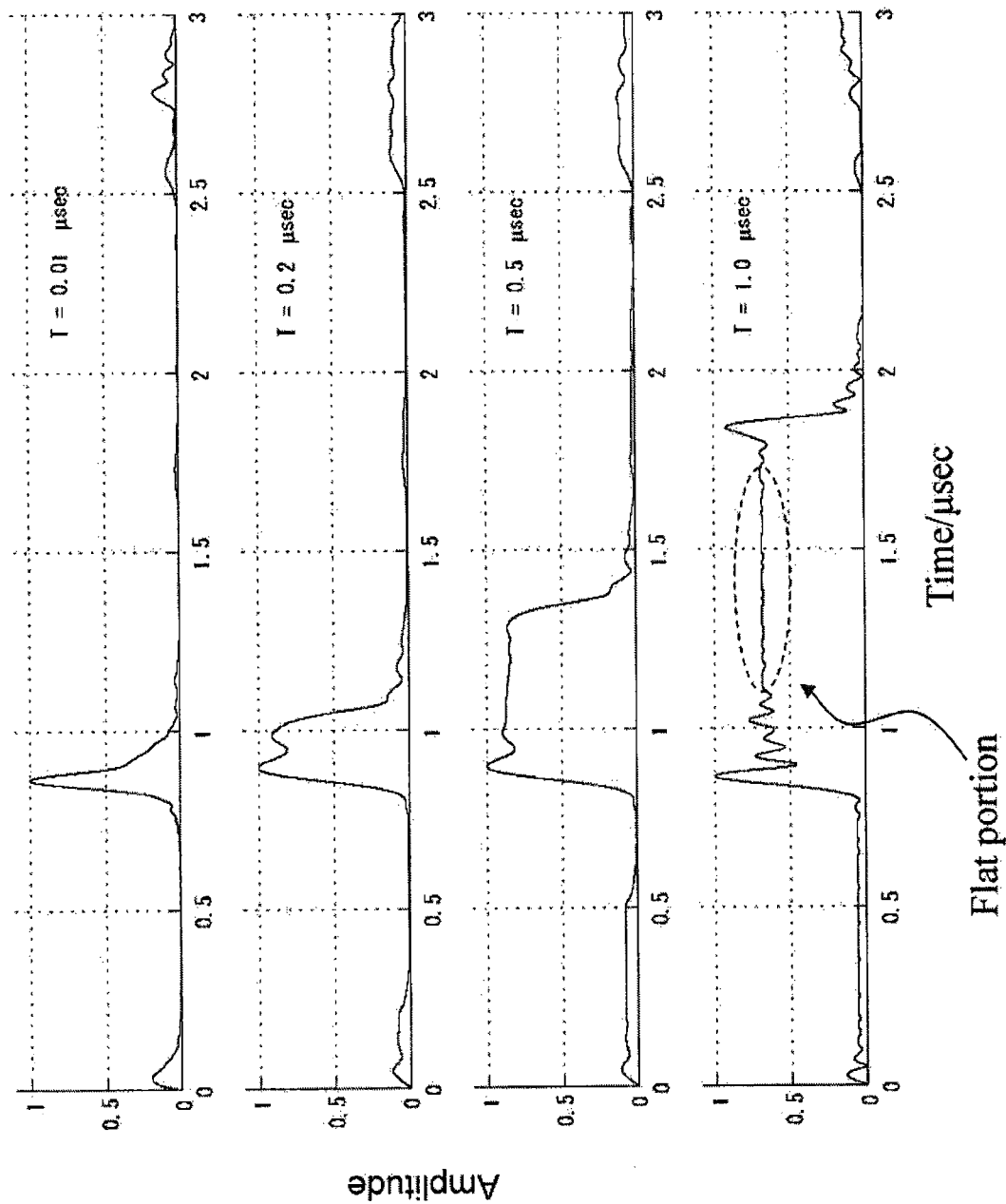
FIGS. 4A and B are graphs showing output signals for different applying times of a high-frequency signal that is input to a SAW sensor.
Figure 4B:
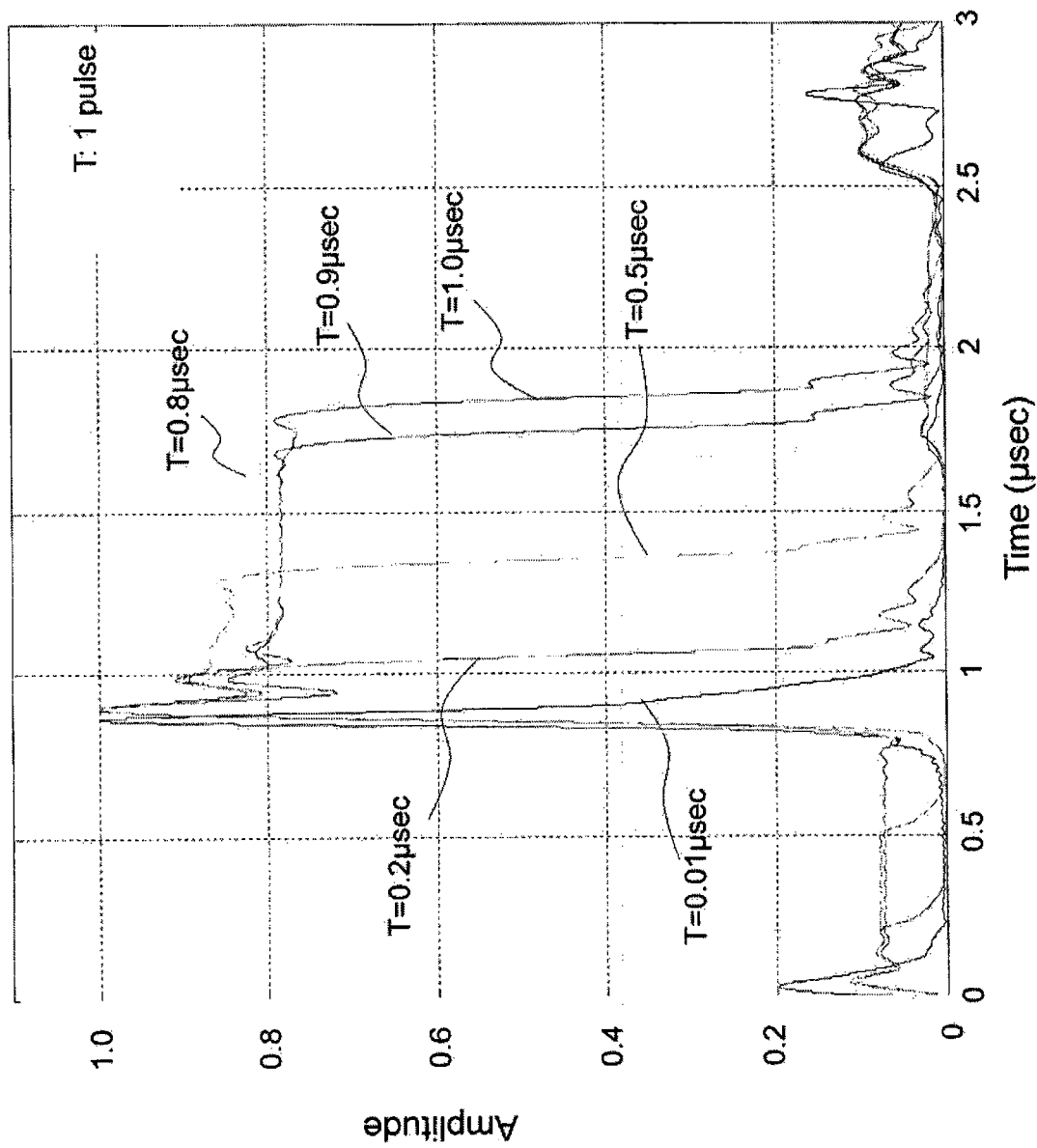

FIGS. 4A and B are graphs showing output signals for different applying times of a high-frequency signal that is input to the SAW sensor. Note that high-frequency signal applying time T is the one pulse signal width. FIG. 4 shows the results of Fourier transformation performed on the signal output from the second IDT 6 for different applying time T of the high-frequency signal that is input to the first IDT 5. More specifically, FIG. 4A contains four plots respectively showing four output signals for four respective high-frequency signal applying time T. FIG. 4B plots the output signals at different applying time so that they are shown in overlapping fashion, and also employs a different scale than that used at FIG. 4A.

The signal profile changes with increasing elapsed time, decreasing from an initially high intensity attributable to additive combination of the main response signal and the direct wave, to a lower intensity attributable only to the main response signal. For long applying time, the intensity having dropped in stepwise fashion to a signal intensity level attributable only to the main response signal, the intensity profile has a flat portion (region) in which signal intensity does not change with elapsed time. What is referred to here as the flat portion is a region in which signal intensity can be treated as constant, inasmuch as it does not change as a function of elapsed time. In particular, it should be constant when subjected to Fourier transformation. More specifically, when applying time is less than or equal to output response time (T=0.01 μsec to T=0.5 μsec), there is no flat portion at which a signal attributable only to the main response signal can be stably identified. For T=0.5 μsec, note that whereas a flat portion may appear to be present at FIG. 4A, when this is enlarged it is found as shown at FIG. 4B that there is no flat portion.

In contradistinction hereto, when applying time exceeds output response time (T=0.8 μsec to T=1.0 μsec), a flat portion can be identified and it is found that the length of the flat portion increases with increasing applying time.

In practice, ripples such as those shown at FIGS. 2A and B are present in the electrical signal output from the second IDT 6. For this reason, although the average level within the flat portion does not change, there may nonetheless be a continuum of periodic peaks present therewithin. That is, there may be small periodic oscillation about some central value, but where this is the case the central value about which the oscillation occurs will remain constant. Note that the term "flat portion" includes both the situation in which the slope of a line drawn through the central values of such oscillations is substantially 0, as well as the situation in which intensities of adjacent peaks are mutually equal.

By analyzing output as a function of applying time, it was moreover found that a stable flat portion could be reliably obtained when one pulse signal width was greater than or equal to a time subtracted the direct wave arrival time from the delay time Furthermore, the one pulse signal applying time may partially overlap the time during which the electrical signal is output from the second IDT 6. In other words, the one pulse signal width may be longer than the delay time. By constituting the one pulse signal in such fashion, it is possible to increase the length of the flat portion.

A signal having the aforementioned constitution will make it possible for the electrical signal that is output from the second IDT 6 to have a flat portion. Where this is the case, it will be possible for electrical signal sampling means 220 to sample at this flat portion, as a result of which it will be possible to stably acquire data by carrying out sampling at a single point. And to the extent that the flat portion is made long, this will make it possible to stably acquire accurate data despite any possible occurrence of error in the timing with which sampling is carried out, thereby improving robustness. Because this makes it unnecessary to carry out sampling over some finite period of time so as to obtain an average value for the output electrical signal, this makes it possible to improve productivity and to acquire data with good precision.

Furthermore, for the one pulse signal that is input thereto, a plurality of sampled values can be reliably obtained by carrying out sampling multiple times within the flat portion. By using the average value of data obtained as a result of such multiple sampling, it will be possible to obtain data of higher accuracy for the one pulse signal that is input thereto, making it possible to improve productivity and to acquire data with good precision.

Note that where pulse width was narrow conventionally as shown at FIG. 3B, the fact that the flat portion was either nonexistent or extremely narrow made it necessary to require that sampling be carried out with highly precise timing, and made it necessary in an attempt to increase data reliability for the high-frequency signal to be input thereto multiple times and for sampling of the electrical signal to be carried out repeatedly.

Furthermore, it is necessary to adopt a RF/IF Gain and Phase Detector which is able to drive in high speed. Such Gain and Phase Detector is a high price and its electric power consumption is huge.

Such sampling by electrical signal sampling means 220 may be carried out after passage of a time which is greater than or equal to the sum of a time corresponding to the signal width of the direct wave and pulse width of the one pulse signal after the start of applying of the one pulse signal. For example, sampling may be carried out after passage of a time which is greater than or equal to the sum of one-half of a time corresponding to the one pulse signal width and the delay time. Carrying out sampling with such timing allows the following two benefits to be obtained. Sampling of the signal can be reliably carried out in the vicinity of the center of the flat portion. Furthermore, because sampling is carried out at a time when the high-frequency signal is no longer being generated, it is possible to divide in time high-frequency signal input and output. This makes it possible to carry out measurement with high accuracy.

Input of the one pulse signal as described above to SAW sensor 100 makes it possible to achieve high accuracy in the detection signal.

While in some embodiments pulse width may be long as described above, in other situations it may be that a long pulse width will cause the one pulse signal from signal generating device 210 to leak into the electrical signal output from second IDT 6.

The SAW sensor 100 is extremely small in size. For this reason, the electrical circuitry for causing the high-frequency signal to be input to the SAW sensor 100 and the electrical circuitry for processing the electrical signal output from SAW sensor 100 are disposed in close mutual proximity. As a result, it may be the case that crosstalk occurs between the two sets of circuitry, and it may be that isolation of neither the input signal nor the output signal can be achieved.

It is also a property of the SAW sensors that losses typically become large when sensitivity is high. It is therefore necessary to increase the accuracy with which the signal (electrical signal) from the SAW sensor 100 is detected and to carry out noise reduction thereon.

Based on the foregoing, pulse width of the one pulse signal may be made equal to a time which is the sum of the delay time and a time corresponding to the full width at half maximum of the single pulse width (the single pulse width/burst pulse width).

Adoption of such constitution makes it possible to cause a flat portion to be present in the electrical signal from the SAW sensor 100, and because isolation thereof can be achieved with respect to the high-frequency signal input to the SAW sensor 100, makes it possible for the SAW sensor 100 to be small in size and high in accuracy.

Specific examples of possible constitutions for the SAW sensor 100 will now be described in detail. The SAW sensor 100 has detector portion 7a, mass of which varies monotonically in correspondence to sorption of target within specimen thereby and/or in correspondence to reaction of such target therewith. In some embodiments, detector portion 7a might be provided with a layer of Au and reactive group fixed to the layer of Au. The reactive group(s) has a reactivity of a type causing occurrence of specific sorption by target. And the layer of Au is preferable because which is relatively unaffected by electrical conductivity and other such electrical properties of the specimen. As it need not be the target themselves that are the object of sorption, reactive group(s) having characteristics which, while reacting the target in the specimen with another substances, will cause to generate a new substance which have a reactivity of a type causing occurrence of specific sorption to the reactive group, might in other embodiments be fixed to a layer of Au. Note that such Au layer may be electrically floating.

Detector portion 7b may function as a reference signal against which the signal detected by detector portion 7a might be compared. In some embodiments, this detector portion 7b of reference signal measuring unit 121 does not have reactivity such as would cause occurrence of specific sorption by target present within specimen or such as would cause structural changes and occurrence of substitution reactions with substance(s) within specimen. More specifically, a layer of Au to which the aforementioned reactive group(s) has not been fixed might be used as detector portion 7b.

FIG. 5 is a perspective view of an exemplary the SAW sensor 100A according to the embodiment of the disclosure. In terms of external appearance, the SAW sensor 100A primarily comprises the piezoelectric substrate 1 and the protective member 3. The Protective member 3 is provided with a first through-hole 18 and a second through-hole 19. The First through-hole 18 may function as specimen inlet. In other words, the first through-hole 18 may function as installation port of the specimens. Second through-hole 19 may function as airhole and/or specimen outlet.

Figure 6:
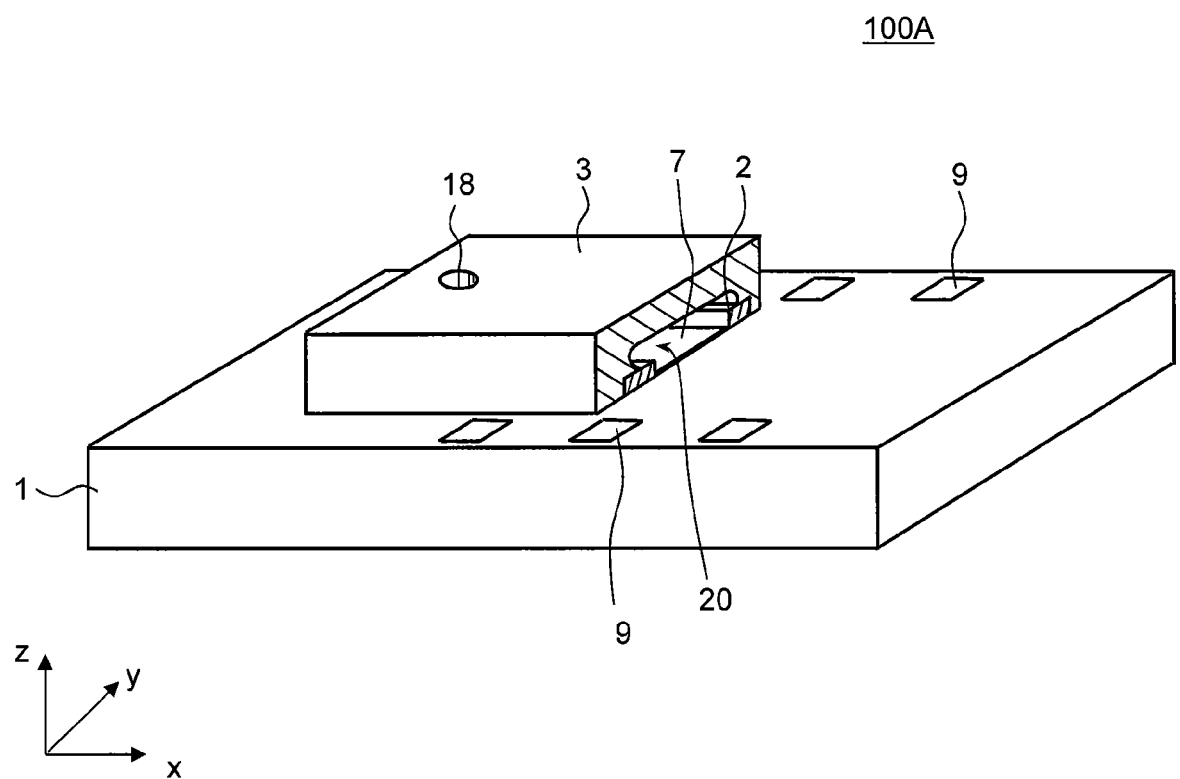
FIG. 6 is a perspective view of the SAW sensor of FIG. 5 showing structure of the interior by removing one side of protective member.

FIG. 6 is a perspective view of SAW sensor 100A of FIG. 5 showing the structure at the interior by removing the protective member 3. Cavity 20 is formed at the interior of protective member 3. Cavity 20 functions as specimen passage to allow flow of specimen therethrough. The First through-hole 18 communicates with cavity 20. That is, specimen entering the first through-hole 18 can flow into and fill cavity 20.

Liquid specimen which flows into cavity 20 includes specimen constituting target, such specimen reacting with the detector portion 7a. The Detector portion 7a comprises a metal layer or the like.

In an embodiment, the piezoelectric substrate 1 contains lithium tantalate ($LiTaO_3$) monocrystal, lithium niobate ($LiNbO_3$) single crystal, quartz, or other such single crystal exhibiting piezoelectricity. In another embodiment, the piezoelectric substrate 1 consists of such single crystal. Planar configuration and various dimensions of the piezoelectric substrate 1 may be set as appropriate. In one embodiment, thickness of piezoelectric substrate 1 is 0.3 mm to 1.0 mm.

Figure 7A:
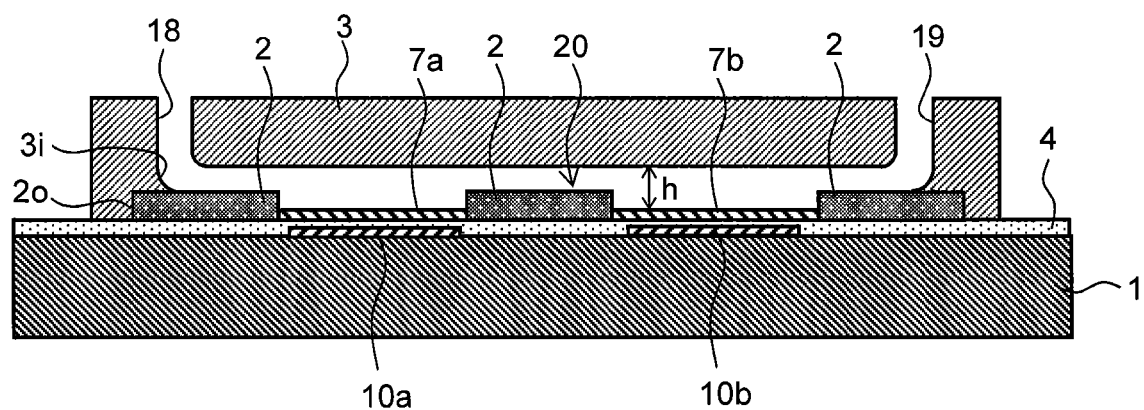
FIG. 7A is a cross sectional view of the SAW sensor along the line XIIa-XIIa in FIG. 5.
Figure 7B:
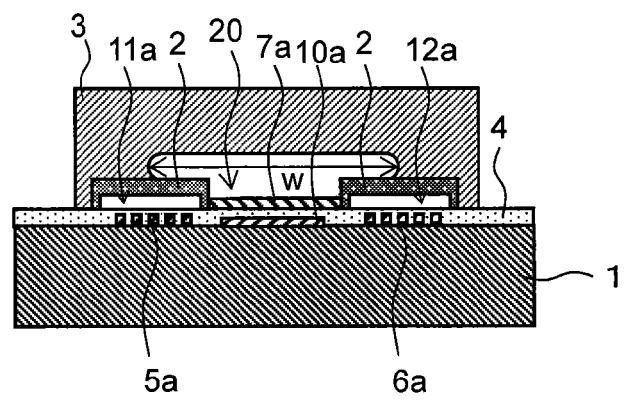
FIG. 7B is an illustration of a cross sectional view of the SAW sensor along the line XIIb-XIIb in FIG. 5.
Figure 8:
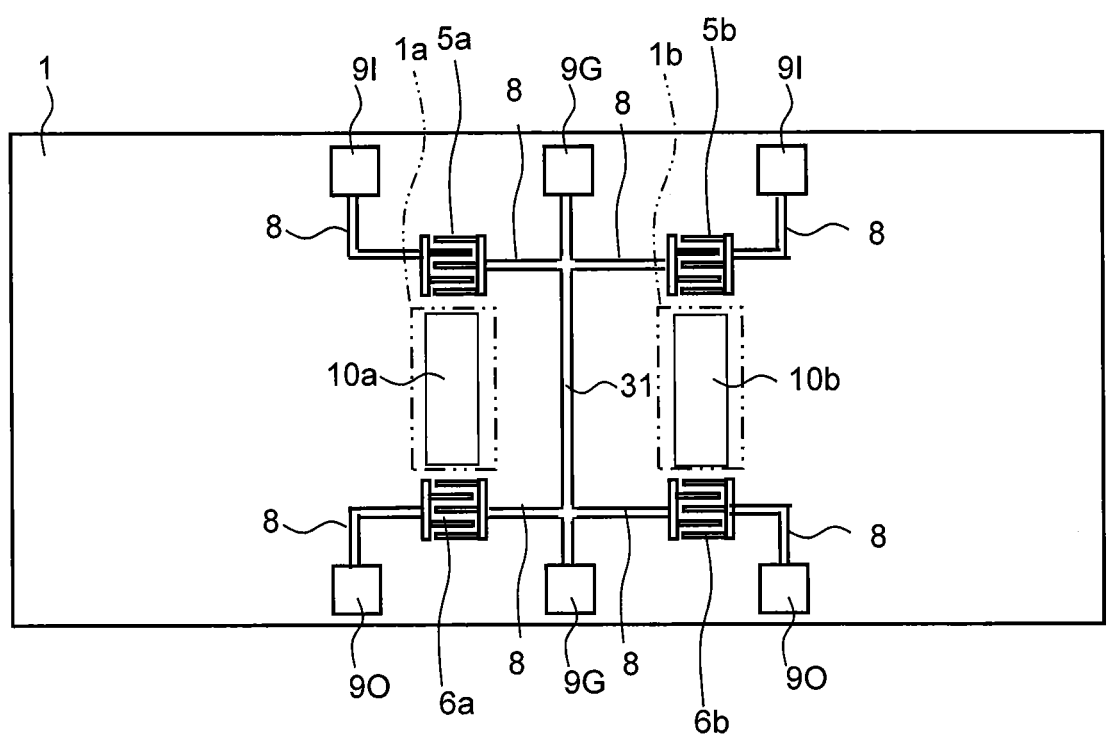
FIG. 8 is a schematic top view of an exemplary SAW sensor.

FIGS. 7A and B show sectional views of SAW sensor 100A. FIG. 7A is a sectional view of section IIVa-IIVa in FIG. 5, and FIG. 7B is a sectional view of section IIVb-IIVb in FIG. 5. FIG. 8 is a top view showing the SAW sensor 100A but in which some components have been omitted from the drawing. More specifically, sheet-like objects 2, protective member 3, and protective layer 4 have been omitted from the drawing.

As shown at FIGS. 7A and B and at FIG. 8, the first IDT 5a, 5b and second IDT 6a, 6b are disposed on the top face of the piezoelectric substrate 1. The First IDT 5a, 5b cause production of a prescribed SAW. The Second IDT 6a, 6b respectively receive the SAW produced by the first IDT 5a, 5b. So as to allow the second IDT 6a to receive the SAW produced by the first IDT 5a, the second IDT 6a is located in the propagation path of the SAW produced by first IDT 5a. Similarly, the second IDT 6b is located in the propagation path of the SAW produced by the first IDT 5b.

Because structures of the first IDT 5b and the second IDT 6b are similar to those of the first IDT 5a and the second IDT 6a, description below will be carried out in terms of the first IDT 5 and the second IDT 6.

As shown in FIG. 1, the first IDT 5 and the second IDT 6 each have a pair of comb electrodes. Each comb electrode (IDT 5, 6) has two mutually opposed busbars, each busbar having a plurality of electrode fingers that extend toward the other busbar. Each pair of comb electrodes is arranged such that the plurality of electrode fingers from each member of the pair is mutually interdigitated. In accordance with one embodiment, the first IDT 5 and the second IDT 6 are transversal IDTs.

Design with respect to frequency characteristics may be carried out using as parameters the number of electrode fingers at the first IDT 5 and the second IDT 6, the distances between adjacent electrode fingers, the length of overlap by interdigitated electrode fingers, and so forth. Among the types of wave which may be excited by IDTs there are Rayleigh waves, Love waves, leaky waves, and so forth. While it is possible to use any type of SAW, the present embodiment employs Love waves.

Acoustic member(s) for suppressing SAW reflection may be provided in region(s) toward the outside in the direction of propagation of the SAW from the first IDT 5. What is referred to here as "region(s) toward the outsider" means outside with respect to the direction in which a SAW would propagate from the first IDT 5 to the second IDT 6. In other words, this means the side of the first IDT 5 that is opposite from the second IDT 6. SAW frequency may for example be set within a range that is from several megahertz (MHz) to several gigahertz (GHz). Within this range, employment in particular of frequency or frequencies of several hundred MHz to 2 GHz is practical and will permit reduction in size of piezoelectric substrate 1, and consequently will make it possible to achieve reduction in size of the SAW sensor 100A.

The First IDT 5 and the second IDT 6 are respectively connected to the lands 9 by way of signal line 8. Signals are input from the exterior to the first IDT 5 by way of these lands 9I and this signal line 8, and signals are output from the second IDT 6 to the exterior by way of these lands 9O and this signal line 8.

Short-circuit electrode 10a is disposed in the first region 1a between the first IDT 5a and the second IDT 6a at the top face of the piezoelectric substrate 1. Similarly, short-circuit electrode 10b is disposed in the second region 1b between the first IDT 5b and the second IDT 6b. The Short-circuit electrodes 10a, 10b are capable of electrically shorting those portions of the top face of piezoelectric substrate 1 that are in SAW propagation paths. The Short-circuit electrodes 10 may permit reduction in SAW losses depending on the type of SAW employed. It is in particular believed that the loss prevention effect due to the short-circuit electrodes 10 will be large when leaky waves are employed as SAWs.

The Short-circuit electrodes 10 may be rectangular in shape, being arranged so as to extend in more or less parallel fashion with respect to the SAWs which are directed toward the second IDT 6 from the first IDT 5. Width of the short-circuit electrode 10 in a direction (x direction) perpendicular to the direction of propagation of the SAW might be made equal to the length of the overlap by the interdigitated electrode fingers of the first IDT 5.

The Short-circuit electrode 10 might be made to float electrically, or a ground-potential the land 9 might be provided, the short-circuit electrode 10 being connected to land 9 which connected to ground-potential so as to cause the short-circuit electrode 10 to be at ground potential. Causing the short-circuit electrode 10 to be at ground potential will make it possible to suppress propagation of the direct wave which is produced due to electromagnetic coupling between the first IDT 5 and the second IDT 6.

The First IDT 5, the second IDT 6, the short-circuit electrodes 10, the signal line 8, and the lands 9 may comprise aluminum, an alloy of aluminum and copper, or the like. In some embodiments, these electrodes may consist of aluminum and/or an alloy of aluminum and copper. Furthermore, these electrodes may be of multilayer construction. Where multilayer construction is employed, the first layer may comprise titanium and/or chromium, and the second layer may comprise aluminum and/or aluminum alloy.

In accordance with one embodiment, the first IDT 5, the second IDT 6, and the short-circuit electrodes 10 are covered by the protective layer(s) 4. The Protective layer 4 might impart antioxidative properties or the like to the respective electrodes and signal line. Protective layer 4 might comprise silicon oxide, aluminum oxide, zinc oxide, titanium oxide, silicon nitride, silicon, and/or the like. In one embodiment, SAW sensor 100A employs silicon dioxide ($SiO_2$) as protective layer 4.

The Protective layer 4 is formed over the entire top face of the piezoelectric substrate 1 except that the lands 9 are exposed. The First IDT 5 and the second IDT 6 are covered by this protective layer 4. This makes it possible to suppress corrosion of IDTs.

In one embodiment, thickness of the protective layer 4 may be 100 nm to 10 μm. Note that the protective layer 4 need not be formed over the entire top face of the piezoelectric substrate 1. For example, only the vicinity of the center of the top face of the piezoelectric substrate 1 might be covered, so as to as to cause a region along the perimeter of the top face of the piezoelectric substrate 1 which includes lands 9 to be exposed.

As shown at FIG. 7B, the first IDT 5 is housed within first oscillation cavity 11, and the second IDT 6 is housed within second oscillation cavity 12. This makes it possible for the first IDT 5 and the second IDT 6 to be isolated from external atmosphere and from the specimen, permitting protection from moisture and other such corrosive substances. Furthermore, establishment of the first oscillation cavity 11 and the second oscillation cavity 12 make it possible for the SAWs at the first IDT 5 and the second IDT 6 to experience large excitations, since they are shielded from disturbances.

The First oscillation cavity 11 and the second oscillation cavity 12 may be formed by bonding the sheet-like objects 2 having concavities for constituting such oscillation cavities to the piezoelectric substrate 1.

The First IDT 5b which function as reference and the second IDT 6b which function as reference are also housed in similar fashion within the first oscillation cavity 11b and the second oscillation cavity 12b.

The First oscillation cavity 11 and the second oscillation cavity 12 of the SAW sensor 100A each occupy a space that is in the shape of a rectangular parallelepiped. Note, however, that the oscillation cavities are not limited to being in the shapes of rectangular parallelepipeds, it being possible to employ cavities that are dome-shaped as seen in sectional view, or elliptical as seen in plan view, or any other suitable variation thereon to accommodate IDT shape or arrangement and so forth.

Penetration(s), which are penetration region(s) in the thickness direction of the sheet-like object(s) 2, are formed in the sheet-like object(s) 2 between concavities for formation of the first oscillation cavity 11 and the second oscillation cavity 12. Such penetration region(s) are provided for formation of detector portion 7a, 7b in SAW propagation paths. That is, when the sheet-like object(s) 2 are bonded to the piezoelectric substrate 1, at least a portion of the propagation paths along which SAWs from the first IDT 5 propagate to the second IDT 6 is exposed by the penetration region(s) as seen in plan view, the detector portion 7a, 7b being formed in such exposed region(s).

The sheet-like object 2 of such configuration might, for example, be formed using photosensitive resist.

The Detector portion 7a, 7b are exposed by penetration region(s) in the sheet-like object(s) 2. The Detector portion 7a comprises metal film. In some embodiments, the detector portion 7a, 7b has a two-layer construction in which there is chromium and there is gold deposited over the chromium. In accordance with one embodiment, aptamer(s) comprising peptide(s) and/or nucleic acid(s) are fixed to the surface of the detector portion 7a. When the liquid specimen comes in contact with the detector portion 7a on which such aptamer(s) have been fixed in this fashion, a particular target within the sample will bind with aptamer(s) corresponding to such target, the Detector portion 7a increasing in monotonic fashion as sorption thereof increases. That is, mass increases monotonically in correspondence to detection of specimen. Note that monotonic increase in the Detector portion 7a occurs only so long as the specimen is being continuously supplied to the detector portion 7a. There is no particular problem when buffer solution is supplied just before or after supply of the specimen with continuous transition therebetween, with the specimen passing over the detector portion 7a and with reduction in mass occurring due to separation of the specimen and the aptamer.

The Detector portion 7b serves as a measuring unit for reference purposes. In accordance with some embodiments, the detector portion 7b has a two-layer lamination in which there is gold deposited over the chromium. So that there is no reactivity with respect to the specimen, no aptamer such as that which may be fixed to the detector portion 7a is attached to the surface of the detector portion 7b. Moreover, surface treatment may be carried out so as to stabilize and lower reactivity with respect to the specimen solution.

To use SAWs to measure properties of the specimen solution and so forth, the one pulse signal of the high-frequency signal is first applied to the first IDT 5 by way of the lands 9I and the signal line 8. Doing this causes the surface of the piezoelectric substrate 1 to be excited in the region where the first IDT 5 is formed and causes a SAW of prescribed frequency to be generated. The SAW which is generated is such that a portion thereof passes through the first region 1a and arrives at the second IDT 6. At this time, at the detector portion 7a which is located in the first region 1a, because aptamer(s) fixed to the detector portion 7a bind to the particular target within the specimen, the Detector portion 7a changing in correspondence to the amount thereof which binds thereto, phase characteristics and so forth of the SAW that passes beneath the detector portion 7a are altered. When the SAW which has characteristics that have been altered in this fashion arrives at the second IDT 6a, an electrical signal which corresponds thereto is produced at the second IDT 6a. The electrical signal is output to the exterior by way of the signal line 8 and the lands 9O, permitting investigation of properties and/or components of the liquid specimen.

Similarly, provided in the same cavity 20 is another detector portion 7b, to which no aptamer has been fixed, the electrical signal output from the second IDT 6b when a signal is input at the second IDT 5b serving as reference signal for calibration to correct for signal fluctuations due to changes in temperature characteristics and the like or humidity and other such ambient conditions.

Conventionally, where SAWs have been used in this fashion to carry out measurements, silicon oxide or other such protective layer for protecting the IDTs and so forth has been provided as has been described. However, if such protective layer is exposed within the passages through which the specimen solution flows, it has been learned that there is increased tendency for occurrence of such problems as reduced detection sensitivity or increased variation in detection sensitivity.

While the cause of such problems is not necessarily clear, it is thought likely that they may be due to occurrence of phenomena such as the fact that if the protective layer 4 is exposed at the penetration region(s), some aptamer might accidentally be made to adhere to the protective layer 4 when aptamer is being fixed to the detector portion 7a, preventing the desired amount of aptamer from being fixed to the detector portion 7a and/or causing target (sample) to adhere to the protective layer 4 when the cavity 20 is filled with liquid specimen.

In some embodiments, the SAW sensor 100A is therefore such that the protective layer 4 is not exposed within the cavity 20 which serves as flow passage.

To make the amount of specimen solution during measurement more uniform, the cavity 20 serving as passage for flow of the specimen solution is provided at the SAW sensor 100A. The Cavity 20 at the SAW sensor 100A is a cavity bounded by the inner surface of the protective member 3, the outer surfaces of the sheet-like objects 2, and the top surfaces of the detector portion 7a, 7b.

Because the volume of the cavity 20 is fundamentally constant, filling the interior of this cavity 20 with the specimen solution makes it possible to cause the amount of the specimen solution at the time of measurement to be made more uniform.

At the SAW sensor 100A, capillary action is utilized during filling of the cavity 20 with the specimen. More specifically, by causing size (diameter and/or the like) of the first through-hole 18 which serves as specimen inlet, and size (width, height, and/or the like) of the cavity 20 which serves as the specimen solution flow passage, to be prescribed values determined based on considerations related to the type of the specimen solution, the material employed at the protective member 3, and so forth, it is possible to drive the specimen from the inlet and toward the flow passage through capillary action. Width w of the cavity 20 shown at FIG. 7B is 0.5 mm to 3 mm in one embodiment, and height h shown at FIG. 7A is 0.05 mm to 0.5 mm in one embodiment. In one embodiment, diameter of the first through-hole 18 might, for example, be 50 µm to 500 µm.

As a result of formation of such the first through-hole 18 and the cavity 20, bringing the specimen into contact with the opening of the first through-hole 18 causes the specimen to thereafter automatically be drawn toward and fill the interior of cavity 20 by capillary action. Consequently, because the SAW sensor 100A is itself equipped with a mechanism for drawing specimen solution thereunto, employment of the SAW sensor 100A makes it possible to cause the specimen to be drawn thereinto without the need to use a pipette or other such equipment. Note that the shape of the first through-hole 18 which serves as the specimen inlet is not limited to being cylindrical. For example, diameter of the first through-hole 18 may gradually decrease as one approaches the cavity 20, or may gradually increase as one approaches the cavity 20, or the opening may be in the shape of a rectangle or other such polygon or may be elliptical. The location at which the first through-hole 18 is formed is not limited to the roof portion of the protective member 3, it being possible for this to be provided at a side wall of the protective member 3.

The Protective member 3 also has the second through-hole 19 in addition to the first through-hole 18. The Second through-hole 19 connects with the cavity 20 and is arranged at a location which is at the opposite end of the protective member 3 from the first through-hole 18. Air that had originally been present within the cavity 20 when the specimen enters the cavity 20 from the first through-hole 18 is effused to the exterior from the second through-hole 19, facilitating entry of the specimen into the interior of the cavity 20.

In one embodiment, corner(s) of portion(s) of the cavity 20 defined by inner surface(s) of the protective member 3 are made rounded. For example, as shown in the sectional views at FIGS. 7A and B, filleting has been carried out where the first through-hole 18 joints with the cavity 20, where second through-hole 19 joints with the cavity 20, and where the inner circumferential surface of the protective member 3 joints with the sheet-like objects 2.

Presence of sharp corners at corner portions of the cavity 20 which serves as flow passage for the specimen causes the specimen solution to collect at such locations and increases the likelihood that the specimen will stagnate. Stagnation of the specimen may, for example, cause concentration of target within the specimen which fills the cavity 20 to vary depending on location, which can lead to reduction in detection sensitivity and so forth. In contradistinction hereto, because corners are rounded at the cavity 20 in the SAW sensor 100A, there is less tendency for the specimen to stagnate, and it is possible to cause concentration of the target within the cavity 20 to be made more uniform.

Furthermore, from the standpoint of preventing stagnation of the specimen, the first through-hole 18 which serves as the specimen inlet should be located as near as possible to the end of the cavity 20.

In one embodiment, the protective member 3 comprises polydimethylsiloxane. In another embodiment, the protective member 3 consists of polydimethylsiloxane. Causing the protective member 3 to comprise polydimethylsiloxane makes it easy to form the protective member 3 so as to have rounded corners or so as to have any other desired shape, and makes it possible to cause the roof and side wall portions of the protective member 3 to be formed in sufficient thickness with relative ease. In accordance with one embodiment, thicknesses of the roof and side wall portions of the protective member 3 are 1 mm to 5 mm.

In accordance with one embodiment, as shown at FIGS. 7A and B, the protective member 3 is bonded to the protective layer 4, which is disposed in peripheral fashion with respect to the sheet-like objects 2, at location(s) where the bottom outer peripheral portion of the protective member 3 comes in contact with the protective layer 4. In other words, the protective member 3 is bonded to the piezoelectric substrate 1 by way of the protective layer 4. When the protective member 3 comprises polydimethylsiloxane and the protective layer 4 comprises $SiO_2$, using oxygen plasma to treat the surface of the protective member 3 that comes in contact with the protective layer 4 will make it possible to easily carry out direct bonding of the protective member 3 and the protective layer 4 without the need to use adhesive or the like. While the reason that the protective member 3 and the protective layer 4 can be directly bonded to each other in this way is not clear, it is believed that it may be due to formation of covalent bonds between Si and O between the protective member 3 and the protective layer 4.

Note that the only difference between the SAW sensor 100 shown in FIG. 1 and the SAW sensor 100A shown in FIGS. 5 through 8 is the arrangement of the lands 9. The SAW sensor 100 shown in FIG. 1 makes it possible to gather the lands 9 together at one side of the piezoelectric substrate 1, facilitating connection to external circuitry. By providing the land 9G, which is connected to reference potential, between the lands 9I, at which the high-frequency signal is input, and the lands 9O, at which the signal is output, it is possible to suppress the influence of crosstalk.

In accordance with the SAW sensor 100A shown in FIG. 8, by providing the lands 9I, at which the high-frequency signal is input, and the lands 9O, at which the signal is output, at respectively different sides of the piezoelectric substrate 1, it is possible to suppress the influence of crosstalk between the two.

Furthermore, as shown in FIGS. 1 and 8, reference potential line 31, which is connected to reference potential, is provided on the piezoelectric substrate 1 between regions which function as the two detectors portion (7). The Reference potential line 31 prevents mutual crosstalk of signals between the two detector portions, making it possible to provide the SAW sensor 100 having high sensitivity.

Note as shown in FIGS. 1 and 8 that, in accordance with some embodiments, the reference potential line 31 is connected to one member of each pair of interdigital electrodes that respectively provided the first IDT 5 and the second IDT 6. That member of each pair of interdigital electrodes respectively provided the first IDT 5 and the second IDT 6 which is connected to the reference potential line 31 is arranged so as to be on the side where the reference potential line 31 is disposed. In other words, at each pair of interdigital electrodes it is the electrode which is located toward the inside that is the one that is connected to reference potential.

Adoption of such constitution makes it possible to efficiently route the signal line 8 and cause the lengths of various segments of the signal line 8 to be made even, making it possible to achieve a more accurate reference signal.

The present invention is not limited to the foregoing embodiments, but may be carried out in a wide variety of modes.

For example, whereas description was carried out at the aforementioned the specimen sensors 100 and 100A in terms of an example in which the detector portions 7a, 7b comprised the metal film 7 and aptamer(s) fixed to the surface of the metal film 7, where the target within the liquid specimen react with the metal film, the constitution may be such that detector portions 7a, 7b are constituted from the metal film 7 alone without use of aptamer(s).

Whereas the aforementioned description was carried out in terms of an example of the specimen detector portions wherein mass increases monotonically in correspondence to reaction with or sorption of the target delivered thereto by the specimen, it is also possible to employ the specimen detector portion(s) wherein mass decreases monotonically in correspondence to reaction with the target delivered thereto by the specimen. Where this is the case, it might be possible, for example, to implement the specimen detector portion(s) by fixing, for example, reactive group(s) having structure(s) displaying reactivity with respect to target and experiencing detachment of portion(s) thereof as a result of reaction with target to the metal film (Au layer) which provides the detector portion 7a. In addition, a positive candidate value for phase shift might be used as the value of the phase shift value when temporal variation in the measured signal obtained using the heterodyne method increases, and a negative candidate value for phase shift might be used as the phase shift value when temporal variation in the measured signal obtained using the heterodyne method decreases. Employment of such a constitution will make it possible to accommodate the specimen detector portions wherein mass increases monotonically in correspondence to reaction with or sorption of the target delivered thereto by the specimen.

Terms and phrases used in this document, and variations hereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future.

Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the present disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent. The term "about" when referring to a numerical value or range is intended to encompass values resulting from experimental error that can occur when taking measurements.

The invention claimed is:

1. A SAW sensor, comprising:
   a piezoelectric substrate;
   a first IDT disposed on a main surface of the piezoelectric substrate and configured to generate a surface acoustic wave when a high-frequency signal is applied thereto;
   a second IDT disposed on the main surface of the piezoelectric substrate and configured to receive the surface acoustic wave from the first IDT and to convert the surface acoustic wave received into an electrical signal that is output therefrom; and
   a detector portion disposed on the main surface of the piezoelectric substrate at a location thereof which is between the first IDT and the second IDT, and configured to cause delay in the surface acoustic wave and to change in mass in correspondence to reaction with and/or sorption of a target provided in a specimen delivered thereto;
   wherein the high-frequency signal is input to the first IDT as a one pulse signal having an applying time that is at least as long as a time subtracted an arrival time of a direct wave attributable to electromagnetic coupling between the first IDT and the second IDT from a delay time of the surface acoustic wave at the detector portion, and that is less than an arrival time at the second IDT of a third response wave of the surface acoustic wave from the first IDT.

2. A SAW sensor according to claim 1, further comprising:
   a protective member that:
      is located on the main surface of the piezoelectric substrate;
      covers the first IDT, the second IDT and the detector portion; and
      comprises a flow passage extending from an installation port to a location above the detector.

3. A SAW sensing device, comprising:
   a SAW sensor according to claim 1; and
   a high-frequency signal generating device that generates the one pulse signal.

4. A SAW sensing device according to claim 3, wherein
   an applying time of the one pulse signal generated by the high-frequency signal generating device partially overlaps a time during which the electrical signal is output from the second IDT.

5. A SAW sensing device according to claim 3, further comprising:
   a sampling unit that carries out sampling of the electrical signal which is output from the second IDT.

6. A SAW sensing device according to claim 5, wherein
   the sampling unit carries out sampling after passage of a time which is greater than or equal to a sum of a time corresponding to a signal width of the direct wave and the applying time of the one pulse signal after a start of applying of the one pulse signal.

7. A SAW sensing device according to claim 5, wherein
   the sampling unit carries out sampling within a region in which a signal is constant and does not change as a function of time when the electrical signal is subjected to Fourier transformation.

\* \* \* \* \*